United States Patent [19]

Stabinsky

[11] Patent Number: 4,652,639
[45] Date of Patent: Mar. 24, 1987

[54] MANUFACTURE AND EXPRESSION OF STRUCTURAL GENES

[75] Inventor: Yitzhak Stabinsky, Boulder, Colo.

[73] Assignee: Amgen, Thousand Oaks, Calif.

[21] Appl. No.: 375,493

[22] Filed: May 6, 1982

[51] Int. Cl.[4] .................. C07H 21/04; C07H 21/02; C12P 21/00; C12P 21/02; C12P 19/34; C12N 15/00; C12N 1/00

[52] U.S. Cl. ........................................ 536/27; 536/28; 536/29; 435/68; 435/70; 435/91; 435/172.3; 435/317; 935/16; 935/17

[58] Field of Search .................... 435/68, 70, 91, 172, 435/253, 317, 172.3; 536/27, 28, 29; 935/16, 17

[56] References Cited

U.S. PATENT DOCUMENTS 4,403,036  9/1983  Hartley et al. ..................... 435/70

FOREIGN PATENT DOCUMENTS 0046039  2/1982  European Pat. Off. ............. 435/68

OTHER PUBLICATIONS

Itakura et al: Science 198, 1056 (1977).
Edge et al: Nature 292, 756 (1981).
Grantham et al: Nucleic Acids Res. 8, 1893 (1980).
Kennell: Progr. Nucl. Acid Res. Mol. Biol. 11, 259 (1971).
Doel et al: Nucleic Acids Research 8, 4575 (1980).
"BRL Restriction Endonuclease Reference Chart", appearing in the '81/'82 Catalog of Bethesda Research Laboratories, Inc., Gaithersburg, Md., pp. 164, 165, and 168.
Goeddel, et al., *Nucleic Acids Research*, 8: 4057–4074 (1980).
Goeddel, et al., *Nature*, 281: 544–548 (1981).
Aharonowitz, et al., *Scientific American*, 245(3): 140–152 (1981).

*Primary Examiner*—Thomas G. Wiseman
*Assistant Examiner*—James Martinell
*Attorney, Agent, or Firm*—Marshall, O'Toole, Gerstein, Murray & Bicknell

[57] ABSTRACT

Described are rapid and highly efficient procedures for the total synthesis of linear, double stranded DNA sequences of up to about 200 base pairs, which sequences may comprise entire structural genes. Illustratively disclosed is the preparation and expression of manufactured genes, including fusion genes, capable of directing synthesis of human β-endorphin and of proteins which differ from human β-endorphin in terms of the identity or relative position of one or more amino acids. Manufactured genes preferably include codons selected from among alternative codons specifying the same amino acid on the basis of preferential expression in a projected host microorganism (e.g., *E. coli*) to be transformed.

7 Claims, 1 Drawing Figure

Segments 5En, 6En, 7En & 8En
↓
Duplex A
↓ Segments 3En & 4En
Duplex B
↓ Segments 9En & 10En
Duplex C
↙ Segments 1En & 2En     ↘ Segments 1'En & 2'En
Duplex D                                Duplex E
↓ 1) Segment 11En                ↓ 1) Segment 11En
  2) EcoRI                                    2) EcoRI
Duplex F                                 Duplex G

MANUFACTURE AND EXPRESSION OF STRUCTURAL GENES

The present invention relates generally to the manipulation of genetic materials and, more particularly, to the manufacture of specific DNA sequences useful in recombinant procedures to secure the production of proteins of interest.

Genetic materials may be broadly defined as those chemical substances which program for and guide the manufacture of constituents of cells and viruses and direct the responses of cells and viruses. A long chain polymeric substance known as deoxyribonucleic acid (DNA) comprises the genetic material of all living cells and viruses except for certain viruses which are programmed by ribonucleic acids (RNA). The repeating units in DNA polymers are four different nucleotides, each of which consists of either a purine (adenine or guanine) or a pyrimidine (thymine or cytosine) bound to a deoxyribose sugar to which a phosphate group is attached. Attachment of nucleotides in linear polymeric form is by means of fusion of the 5' phosphate of one nucleotide to the 3' hydroxyl group of another. Functional DNA occurs in the form of stable double stranded associations of single strands of nucleotides (known as oligodeoxynucleotides), which associations occur by means of hydrogen bonding between purine or pyrimidine bases [i.e., "complementary" associations existing either between adenine (A) and thymine (T) or guanine (G) and cytosine (C)]. By convention, nucleotides are referred to by the names of their constituent purine or pyrimidine bases, and the complementary associations of nucleotides in double stranded DNA (i.e., A-T and G-C) are referred to as "base pairs". Ribonucleic acid is a polynucleotide comprising adenine, guanine, cytosine and uricil (U), rather than thymine, bound to ribose and a phosphate group.

Most briefly put, the programming function of DNA is generally effected through a process wherein specific DNA nucleotide sequences (genes) are "transcribed" into relatively unstable messenger RNA (mRNA) polymers. The mRNA, in turn, serves as a template for the formation of structural, regulatory and catalytic proteins from amino acids. This translation process involves the operations of small RNA strands (tRNA) which transport and align individual amino acids along the mRNA strand to allow for formation of polypeptides in proper amino acid sequences. The mRNA "message", derived from DNA and providing the basis for the tRNA supply and orientation of any given one of the twenty amino acids for polypeptide "expression", is in the form of triplet "codons" — sequential groupings of three nucleotide bases. In one sense, the formation of a protein is the ultimate form of "expression" of the programmed genetic message provided by the nucleotide sequence of a gene.

Certain DNA sequences which usually "precede" a gene in a DNA polymer provide a site for initiation of the transcription into mRNA. These are referred to as "promoter" sequences. Other DNA sequences, also usually "upstream" of (i.e., preceeding) a gene in a given DNA polymer, bind proteins that determine the frequency (or rate) of transcription initiation. These other seqeunces are referred to as "regulator" sequences. Thus, sequences which precede a selected gene (or series of genes) in a functional DNA polymer and which operate to determine whether the transcription (and eventual expression) of a gene will take place are collectively referred to as "promoter/regulator" or "control" DNA sequences. DNA sequences which "follow" a gene in a DNA polymer and provide a signal for termination of the transcription into mRNA are referred to as "terminator" sequences.

A focus of microbiological processing for nearly the last decade has been the attempt to manufacture industrially and pharmaceutically significant substances using organisms which do not intially have genetically coded information concerning the desired product included in their DNA. Simply put, a gene that specifies the structure of a product is either isolated from a "donor" organism or chemically synthesized and then stably introduced into another organism which is preferably a self-replicating unicellular microorganism. Once this is done, the existing machinery for gene expression in the "transformed" host cells operates to construct the desired product.

The art is rich in patent and literature publications relating to "recombinant DNA" methodologies for the isolation, synthesis, purification and amplification of genetic materials for use in the transformation of selected host organisms. U.S. Pat. No. 4,237,224 to Cohen, et al., for example, relates to transformation of procaryotic unicellular host organisms with "hybrid" viral or circular plasmid DNA which includes selected exogenous DNA sequences. The procedures of the Cohen, et al. patent first involve manufacture of a transformation vector by enzymatically cleaving viral or circular plasmid DNA to form linear DNA strands. Selected foreign DNA strands are also prepared in linear form through use of similar enzymes. The linear viral or plasmid DNA is incubated with the foreign DNA in the presence of ligating enzymes capable of effecting a restoration process and "hybrid" vectors are formed which include the selected foreign DNA segment "spliced" into the viral or circular DNA plasmid.

Transformation of compatible unicellular host organisms with the hybrid vector results in the formation of multiple copies of the foreign DNA in the host cell population. In some instances, the desired result is simply the amplification of the foreign DNA and the "product" harvested is DNA. More frequently, the goal of transformation is the expression by the host cells of the foreign DNA in the form of large scale synthesis of isolatable quantities of commercially significant protein or polypeptide fragments coded for by the foreign DNA. See also, e.g., U.S. Pat. Nos. 4,264,731 (to Shine), 4,273,875 (to Manis) and 4,293,652 (to Cohen).

The success of procedures such as described in the Cohen, et al. patent is due in large part to the ready availability of "restriction endonuclease" enyzmes which facilitate the site-specific cleavage of both the unhybridized DNA vector and, e.g., eukaryotic DNA strands containing the foreign sequences of interest. Cleavage in a manner providing for the formation of single stranded complementary "ends" on the double stranded linear DNA strands greatly enhances the likelihood of functional incorporation of the foreign DNA into the vector upon "ligating" enzyme treatment. A large number of such restriction endonuclease enzymes are currently commercially available. [See, e.g., "BRL Restriction Endonuclease Reference Chart" appearing in the "'81/'82 Catalog" of Bethesda Research Laboratories, Inc., Gaithersburg, Maryland.]Verification of hybrid formation is facilitated by chromatographic techniques which can, for example, distinguish the hybrid plasmids from non-hybrids on the basis of molecular weight. Other useful verification techniques involve radioactive DNA hybridization.

Another manipulative "tool" largely responsible for successes in transformation of procaryotic cells is the use of selectable "marker" gene sequences. Briefly put, hybrid vectors are employed which contain, in addition to the desired foreign DNA, one or more DNA sequences which code for expression of a phenotypic trait capable of distinguishing transformed from non-transformed host cells. Typical marker gene sequences are those which allow a transformed procaryotic cell to survive and propagate in a culture medium containing metals, antibiotics, and like components which would kill or severely inhibit propagation of non-transformed host cells.

Successful expression of an exogenous gene in a transformed host microorganism depends to a great extent on incorporation of the gene into a transformation vector with a suitable promoter/regulator region present to insure transcription of the gene into mRNA and other signals which insure translation of the mRNA message into protein (e.g., ribosome binding sites). It is not often the case that the "original" promoter/regulator region of a gene will allow for high levels of expression in the new host. Consequently, the gene to be inserted must either be fitted with a new, host-accommodated transcription and translation regulating DNA sequence prior to insertion or it must be inserted at a site where it will come under the control of an existing promoter/-regulator region in the vector DNA.

It is frequently the case that the insertion of an exogenous gene into, e.g., a circular DNA plasmid vector, is performed at a site either immediately following an extant transcription and translation signal or within an existing plasmid-borne gene coding for a rather large protein which is the subject of high degrees of expression in the host. In the latter case, the host's expression of the "fusion gene" so formed results in high levels of production of a "fusion protein" including the desired protein sequence (e.g., as an intermediate segment which can be isolated by chemical cleavage of large protein). Such procedures not only insure desired regulation and high levels of expression of the exogenous gene product but also result in a degree of protection of the desired protein product from attack by proteases endogenous to the host. Further, depending on the host organism, such procedures may allow for a kind of "piggyback" transportation of the desired protein from the host cells into the cell culture medium, eliminating the need to destroy host cells for the purpose of isolating the desired product.

While the foregoing generalized descriptions of published recombinant DNA methodologies may make the processes appear to be rather straightforward, easily performed and readily verified, it is actually the case that the DNA sequence manipulations involved are quite painstakingly difficult to perform and almost invariably characterized by very low yields of desired products.

As an example, the initial "preparation" of a gene for insertion into a vector to be used in transformation of a host microorganism can be an enormously difficult process, especially where the gene to be expressed is endogenous to a higher organism such as man. One laborious procedure practiced in the art is the systematic cloning into recombinant plasmids of the total DNA genome of the "donor" cells, generating immense "libraries" of transformed cells carrying random DNA sequence fragments which must be individually tested for expression of a product of interest. According to another procedure, total mRNA is isolated from high expression donor cells (presumptively containing multiple copies of mRNA coded for the product of interest), first "copied" into single stranded cDNA with reverse transcriptase enzymes, then into double stranded form with polymerase, and cloned. The procedure again generates a library of transformed cells somewhat smaller than a total genome library which may include the desired gene copies free of non-transcribed "introns" which can significantly interfere with expression by a host microorganism. The above-noted time-consuming gene isolation procedures were in fact employed in published recombinant DNA procedures for obtaining microorganism expression of several proteins, including rat proinsulin [Ullrich, et al., Science, 196, 1313-1318 (1977)], human fibroblast interferon [Goeddel, et al., Nucleic Acids Research, 8, pp. 4057-4074 (1980)] mouse $\beta$-endorphin [Shine, et al. Nature, vol. 285, pp. 456-461 (1980)] and human leukocyte interferon [Goeddel, et al., Nature, 287, pp. 411-416 (1980) and Godell, et al., Nature 290, pp. 20-26 (1981)].

Whenever possible, the partial or total manufacture of genes of interest from nucleotide bases constitutes a much preferred procedure for preparation of genes to be used in recombinant DNA methods. A requirement for such manufacture is, of course, knowledge of the correct amino acid sequence of the desired polypeptide. With this information in hand, a generative DNA sequence code for the protein (i.e., a properly ordered series of base triplet codons) can be planned and a corresponding synthetic, double stranded DNA segment can be constructed. A combination of manufacturing and cDNA synthetic methodologies is reported to have been employed in the generation of a gene for human growth hormone. Specifically, a manufactured linear double stranded DNA sequence of 72 nucleotide base pairs (comprising codons specifying the first 24 amino acids of the desired 191 amino acid polypeptide) was ligated to a cDNA-derived double strand coding for amino acids Nos. 25-191 and inserted in a modified pBR322 plasmid at a locus controlled by a lac promotor/regulator sequence. [Goeddel, et al., Nature, 281, pp. 544-548 (1981)]

Completely synthetic procedures have been employed for the manufacture of genes coding for relatively "short" biologically functional polypeptides, such as human somatostatin (14 amino acids) and human insulin (2 polypeptide chains of 21 and 30 amino acids, respectively).

In the somatostatin gene preparative procedure [Itakura, et al., Science, 198, pp. 1056-1063 (1977)] a 52 base pair gene was constructed wherein 42 base pair represented the codons specifying the required 14 amino acids and an additional 10 base pairs were added to permit formation of "sticky-end" single stranded terminal regions employed for ligating the structural gene into a microorganism transformation vector. Specifically, the gene was inserted close to the end of a $\beta$-galactosidase enzyme gene and the resultant fusion gene was expressed as a fusion protein from which somatostatin was isolated by cyanogen bromide cleavage. Manufacture of the human insulin gene, as noted above, involved preparation of genes coding for a 21 amino acid chain and for a 30 amino acid chain. Eighteen oligodeoxynucleotide fragments were combined to make the gene for the longer chain, and eleven fragments were joined into a gene for the shorter chain. Each gene was employed to form a fusion gene with a β-galactosidase gene and the individually expressed polypeptide chains were enzymatically isolated and linked to form complete insulin molecules. [Goeddel, et al., *Proc. Nat. Acad. Sci. U.S.A.*, 76, pp. 106–110 (1979).]

In each of the above procedures, oligodeoxynucleotide segments were prepared, and then sequentially ligated according to the following general procedure. [See, e.g., Argarwal, et al., *Nature*, 227, pp. 1–7 (1970) and Khorana, *Science*, 203, pp. 614–675 (1979)] An initial "top" (i.e., 5'–3' polarity) oligodeoxynucleotide segment is enzymatically joined to a second "top" segment. Alignment of these two "top stands is made possible using a "bottom" (i.e., 3' to 5' polarity) strand having a base sequence complementary to half of the first top strand and half of the second top strand. After joining, the uncomplemented bases of the top strands "protrude" from the duplex portion formed. A second bottom strand is added which includes the five or six base complement of a protruding top strand, plus an additional five or six bases which then protrude as a bottom single stranded portion. The two bottom strands are then annealed. Such sequential additions are continued until a complete gene sequence is developed, with the total procedure being very time consuming and highly inefficient.

The time-consuming characteristics of such methods for total gene synthesis are exemplified by reports that three months' work by at least four investigators was needed to perform the assembly of the two "short", insulin genes previously referred to. Further, while only relatively small quantities of any manufactured gene are needed for success of vector insertion, the above synthetic procedures have such poor overall yields (on the order of 20% per ligation) that the eventual isolation of even minute quantities of a selected short gene is by no means guaranteed with even the most scrupulous adherence to prescribed methods. The maximum length gene which can be synthesized is clearly limited by the efficiency with which the individual short segments can be joined. If n such ligation reactions are required and the yield of each such reaction is y, the quantity of correctly synthesized genetic material obtained will be proportional to $y^n$. Since this relationship is expotential in nature, even a small increase in the yield per ligation reaction will result in a substantial increase in the length of the largest gene that may be synthesized.

Inefficiencies in the above-noted methodology are due in large part to the formation of undesired intermediate products.

Further, the longer the individual oligodeoxynucleotides are, the more likely it is that they will form thermodynamically stable self-associations such as "hairpins" or aggregations.

Proposals for increasing synthetic efficiency have not been forthcoming and it was recently reported that, "With the methods now available, however, it is not economically practical to synthesize genes for peptides longer than about 30 amino acid units, and many clinically important proteins are much longer". [Aharonowitz, et al. *Scientific American*, 245, No. 3, pp. 140–152, at p. 151 (1981).]

An illustration of the "economic practicalities" involved in large gene synthesis is provided by the recent publication of successful efforts in the total synthesis of a human leukocyte interferon gene. [Edge, et al., *Nature*, 292, pp. 756–782 (1981)] Briefly summarized, 67 different oligodeoxynucleotides containing about 15 bases were synthesized and joined in the "50 percent overlap" procedure of the type noted above to form eleven short duplexes. These, in turn were assembled into four longer duplexes which were eventually joined to provide a 514 base pair gene coding for the 166 amino acid protein. The procedure, which the authors characterize as "rapid", is reliably estimated to have consumed nearly a year's effort by five workers and the efficiency of the assembly strategy was clearly quite poor. It may be noted, for example, that while 40 pmole of each of the starting 67 oligodeoxynucleotides was prepared and employed to form the eleven intermediate-sized duplexes, by the time assembly of the four large duplexes was achieved, a yield of only about 0.01 pmole of the longer duplexes could be obtained for use in final assembly of the whole gene.

There exists, therefore, a need in the art for rapid, efficient and economical methods for the manufacture of structural genes capable of directing the synthesis of polypeptides of a size in excess of about 30 amino acids.

Another aspect of the practice of recombinant DNA techniques for the expression, by microorganisms, of proteins of industrial and pharmaceutical interest is the phenomenon of "codon preference". While it was earlier noted that the existing machinery for gene expression in genetically transformed host cells will "operate" to construct a given desired product, levels of expression attained in a microorganism can be subject to wide variation, depending in part on specific alternative forms of the amino acid-specifying genetic code present in an inserted exogenous gene. A "triplet" codon of four possible nucleotide bases can exist in 64 variant forms. That these forms provide the message for only 20 different amino acids (as well as translation initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist a variable natural hierarchy or "preference" for certain codons in certain types of cells.

As one example, the amino acid leucine is specified by any of six DNA codons including CTA, CTC, CTG, CTT, TTA, and TTG (which correspond, respectively, to the mRNA codons, CUA, CUC, CUG, CUU, UUA and UUG). Exhaustive analysis of genome codon frequencies for microorganisms has revealed endogenous DNA of *E. coli* bacteria most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an *E. coli* host will depend to some extent on the frequency of codon use. For example, a gene rich in TTA codons will in all probability be poorly expressed in *E. coli*, whereas a CTG rich gene will probably highly express the polypeptide. In a like manner, when yeast cells are the projected transformation host cells for expression of a leucine-rich polypeptide, a preferred codon for use in an inserted DNA would be TTA. See, e.g., Grantham, et al. *Nucleic Acids Research*, 8, pp. r49–r62 (1980); Grantham, et al., *Nucleic Acids Research*, 8, pp.

1893-1912 (1980); and, Grantham, et al., *Nucleic Acids Research*, 9, pp. r43-r74 (1981).

The implications of codon preference phenomena on recombinant DNA techniques are manifest, and the phenomenon may serve to explain many prior failures to achieve high expression levels for exogenous genes in successfully transformed host organisms—a less "preferred" codon may be repeatedly present in the inserted gene and the host cell machinery for expression may not operate as efficiently. This phenomenon directs the conclusion that wholly manufactured genes which have been designed to include a projected host cell's preferred codons provide a preferred form of foreign genetic material for practice of recombinant DNA techniques. In this context, the absence of procedures for rapid and efficient total gene manufacture which would permit codon selection is seen to constitute an even more serious roadblock to advances in the art.

Of substantial interest to the background of the present invention is the state of the art with regard to the preparation and use of a class of biologically active, analgesic substances known as β-endorphins. These compounds, originally isolated from pituitary tissue of various mammalian and avian species, are 31 amino acid polypeptides having similar primary structures which differ from each other in terms of only a few amino acid residues. For example, the amino acid sequence of human β-endorphin ($\beta_h$-EP) is reported as:

and mouse β-endorphin differs from the human form in having a [His$^{27}$] rather than [Tyr$^{27}$] residue. The β-endorphins can, of course, be synthesized in small quantities by the well-known Merrifield procedure [Merrifield, *J. Am. Chem. Soc.*, 85, pp. 2149-2154 (1963)], and such methods have recently been employed to prepare $\beta_h$-[Trp$^{27}$]-EP and a 2-nitrophenylsulfenyl derivative thereof.

Recombinant DNA technology has been used to isolate and express the gene for mouse β-endorphin. [Agarwal, et al., *Nature*, 227, pp. 1-7 (1970)] The gene was cloned and expressed in *E. coli* as a fused β-galactosidase-β-endorphin protein. The general protocol for preparing the gene was as follows. The gene was isolated from a cloned DNA (cDNA) fragment derived by reverse transcription of mRNA coding for the mouse ACTH/β-LPH precursor protein. An appropriate HpaII and HindIII restriction endonuclease fragment was isolated from the cloned DNA segment. This fragment contained the gene for mouse β-endorphin and part of the gene for mouse β-MSH. After a further series of reactions and isolations, a fragment containing only the desired gene was obtained. This gene was then inserted into an appropriate plasmid containing the gene for β-galactosidase and the hybrid plasmid was used for *E. coli* transformation. This resulted in the production of a fusion protein containing both β-galactosidase and mouse β-endorphin. β-endorphin was isolated free of β-galactosidase by treating the fusion protein with citraconic anhydride followed by a treatment with tryspin. The mouse δ-endorphin isolated by this procedure was biologically active. In addition to the [His$^{27}$] residue, the mouse δ-endorphin product differed from human β-endorphin in that it contained an extra amino acid, an amino terminal arginine.

Despite the significant pharmaceutical potential of human β-endorphin as an analgesic agent, there have been no reports of the use of recombinant DNA techniques for the large scale production of this substance or its structural analogs. More particularly, there are no reports of either the manufacture of a synthetic $\beta_h$-EP gene (or any synthetic gene directing the expression of a polypeptide which differs from $\beta_h$-EP in terms of the identity or relative position of one or more amino acid residues) or of the production of $\beta_h$-EP protein by any recombinant DNA technique.

BRIEF SUMMARY

The present invention provides novel, rapid and highly efficient procedures for the total manufacture of linear, double stranded DNA sequences of up to about 200 nucleotide base pairs, which sequences may comprise entire structural genes capable of directing the synthesis of a wide variety of polypeptides of interest.

DNA sequences are manufactured from nucleotide bases by a general method comprising the steps of:

(1) preparing two or more different, linear, duplex DNA strands, each duplex strand including a double stranded region of 12 or more selected complementary base pairs and further including a top single stranded terminal sequence of from 3 to 7 selected bases at one end of the strand and/or a bottom single stranded terminal sequence of from 3 to 7 selected bases at the other end of the strand, each single stranded terminal sequence of each duplex DNA strand comprising the entire base complement of at most one single stranded terminal sequence of any other duplex DNA strand prepared; and (2) annealing each duplex DNA strand prepared in step (1) to one or two different duplex strands prepared in step (1) having a complementary single stranded terminal sequence, thereby to form a single continuous double stranded DNA sequence which has a duplex region of at least 27 selected base pairs including at least 3 base pairs formed by complementary association of single stranded terminal sequences of duplex DNA strands prepared in step (1) and which has from 0 to 2 single stranded top or bottom terminal regions of from 3 to 7 bases.

In a preferred embodiment of the general process, at least three different duplex DNA strands are prepared in step (1) and all strands so prepared are annealed concurrently in a single annealing reaction mixture to form a single continuous double stranded DNA sequence which has a duplex region of at least 42 selected base pairs including at least two non-adjacent sets of 3 or more base pairs formed by complementary association of single stranded terminal sequences of duplex strands prepared in step (1).

The duplex DNA strand preparation step (1) preferably comprises the steps of:

(a) constructing first and second linear oligodeoxynucleotide segments having 15 or more bases in a selected linear sequence, the linear sequence of bases of the second segment comprising the total complement of the sequence of bases of the first segment except that at least one end of the second segment shall either include an additional linear sequence of from 3 to 7 selected bases beyond those fully complementing the first segment, or shall lack a linear sequence of from 3 to 7 bases complementary to a terminal sequence of the first segment, provided, however, that the second segment shall not have an additional sequence of bases or be lacking a sequence of bases at both of its ends; and, (b) combining the first and second segments under conditions conducive to complementary association between segments to form a linear, duplex DNA strand.

In a highly preferred embodiment of the invention, the sequence of bases in the double stranded DNA sequence formed includes one or more triplet codons selected from among alternative codons specifying the same amino acid on the basis of preferential expression characteristics of the codon in a projected host microorganism, such as yeast cells or bacteria, especially E. coli bacteria.

Also provided by the present invention are novel manufactured genes including, for example, new genes and fusion genes capable of directing the synthesis of human β-endorphin as well as numerous analogs of human 8-endorphin which differ from the authentic protein in terms of the identity or relative position of one or more amino acids. A variety of protein products generated by the expression of the new genes is also provided by the invention.

Other aspects and advantages of the present invention will be apparent upon consideration of the following detailed description thereof.

DETAILED DESCRIPTION

As employed herein, the term "manufactured" as applied to a DNA sequence or gene shall designate a product either totally chemically synthesized by assembly of nucleotide bases or derived from the biological replication of a product thus chemically synthesized. As such, the term is exclusive of products "synthesized" by cDNA methods or genomic cloning methodologies which involve starting materials which are initially of biological origin. The following abbreviations shall be employed herein to designate amino acids: Alanine, Ala; Arginine, Arg; Asparagine, Asn; Aspartic acid, Asp; Cysteine, Cys; Glutamine, Gln; Glutamic acid, Glu; Glycine, Gly; Histidine, His; Isoleucine, Ile; Leucine, Leu; Lysine, Lys; Methionine, Met; Phenylalanine, Phe; Proline, Pro; Serine, Ser; Threonine, Thr; Tryptophan, Trp; Tyrosine, Tyr; Valine, Val. The following abbreviations shall be employed for nucleotide bases: A for adenine; G for guanine; T for thymine; U for uracil; and C for cytosine.

For ease of understanding of the present invention, Table I below provides a tabular correlation between the 64 alternate triplet nucleotide base codons of DNA and the 20 amino acids and transcription termination ("Stop") function specified thereby.

TABLE I

| FIRST POSITION | SECOND POSITION | | | | THIRD POSITION |
|---|---|---|---|---|---|
| | T | C | A | G | |
| T | Phe | Ser | Tyr | Cys | T |
| | Phe | Ser | Tyr | Cys | C |
| | Leu | Ser | Stop | Stop | A |
| | Leu | Ser | Stop | Trp | G |
| C | Leu | Pro | His | Arg | T |
| | Leu | Pro | His | Arg | C |

TABLE I-continued

| FIRST POSITION | SECOND POSITION | | | | THIRD POSITION |
|---|---|---|---|---|---|
| | T | C | A | G | |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Gal | Ala | Glu | Gly | G |

Once the structure of the desired polypeptide is determined, practice of the present invention involves: the manufacture of a specific, continuous double stranded DNA comprising up to about 200 base pairs which codes for the protein; the insertion of the manufactured sequence into an appropriate microorganism transformation vector; and, the transformation of a selected microorganism host with the vector. The synthesized DNA sequence may be provided with a promotor/regulator region for autonomous control of expression or may be incorporated into the vector in a manner providing for control of expression by a promotor/regulator sequence extant in the vector. The manufactured DNA sequence may also be incorporated into an intermediate position along an existing gene in the vector (forming a fusion gene) and may thus be expressed in the form of a fusion protein.

In the practice of the invention in its preferred forms, the polypeptide produced may vary in size from about 15 to 20 amino acids up to about 70 amino acids. High levels of expression of the desired polypeptide by selected transformed host organisms is facilitated through the manufacture of DNA sequences which include one or more alternative codons which are preferentially expressed by the host.

Rapid and highly efficient manufacture of double stranded DNA sequences specifying synthesis of selected polypeptides is accomplished by means of a unique procedure involving the assembly from oligodeoxynucleotides of two or more different, linear, duplex DNA strands each including a relatively long 12 or more base pair) double stranded region along with a relatively short (3 to 7 base) single stranded region on one or both opposing ends of the double strand. In preferred practices of the invention, duplexes with double stranded regions of from about 14 to 50 base pairs are formed, with the most preferred duplex forms including from 18 to 30 base pairs in the double stranded region. Even when duplexes used have double stranded regions of only about 12 base pairs in length, single stranded will ordinarily not exceed one third the length of the double stranded regions.

The double stranded regions are designed to include codons needed to specify assembly of an initial, or terminal or intermediate portion of the total amino acid sequence of the desired polypeptide. Where possible, alternative codons preferentially expressed by a projected host (e.g., E. coli) are employed. It is a significant benefit of the procedures of the present invention that they allow greater flexibility in codon selection.

Depending on the relative position to be assumed in the finally assembled DNA sequence, the single stranded region(s) of the duplex strands employed will include a sequence of bases which, when complemented by bases of other duplex strands, also provide codons specifying amino acids within the desired polypeptide sequence.

Duplex strands formed according to the invention are then enzymatically joined to the one or two different duplex strands having complementary short, single stranded regions to form a desired continuous double stranded DNA sequence which codes for the desired polypeptide. The sequence so formed may provide all or part of a structural gene. It may have one or more "blunt" or "sticky" ends and may also include promotor/regulator regions.

High efficiencies and rapidity in total sequence assembly are augmented by performing a single annealing reaction involving three or more duplex strands, the short, single stranded regions of which constitute the base complement of at most one other single stranded region of any other duplex strand. Providing all duplex strands formed with short single stranded regions which uniquely complement only one of the single stranded regions of any other duplex is accomplished by alternative codon selection within the context of genetic code redundancy, and preferably also in the context of codon preferences of the projected host organism.

Following are illustrative examples of the practice of the invention in formation of manufactured genes capable of directing the synthesis of authentic human $\beta$-endorphin and biologically functional polypeptide analogs thereof. It will be apparent from these examples that the gene manufacturing methodology of the present invention provides, for the first time, an overall synthetic strategy for the truly rapid, efficient synthesis and expression of genes within a highly flexible framework allowing for controlled variations in the structures of products expressed which has never before been available to investigators practicing recombinant DNA techniques.

The following example illustrates the general procedures for the synthesis of oligodeoxynucleotides useful in the manufacture of gene of interest, such as that directing the synthesis of authentic $\beta_h$-EP.

EXAMPLE 1

Preparation of oligodeoxynucleotides for use in manufacture of a DNA sequence comprising a gene for human $\beta$-endorphin is carried out according to the general methodologies published in Mutteucci, et al., *J. Am. Chem. Soc.*, 103, pp. 3185–3192 (1981) and Beaucage, et al., *Tetrahedron Letters*, 22, pp. 1859-1862 (1981) and the references cited therein. The synthesis begins by derivatizing high performance liquid chromatography grade silica gel to contain appropriately protected nucleotides. The oligodeoxynucleotides are linked through the 3'- hydroxyl group to a carboxylic acid functional group attached covalently to the silica gel. The chemical steps used for the addition of one nucleotide to this support are as follows: (1) detritylation using $ZnBr_2$ in nitromethane/methanol (4 min.); (2) condensation of a 5'-di-p-anisylphenylmethyl deoxynucleoside 3'-methoxy-N, N-diemthylaminophosphine with the support bound nucleoside (5 min.); (3) blocking unreacted support bound nucleoside hydroxyl groups with acetic anhydride (5 min.); and (4) oxidation of the phophite to the phosphate with $I_2$ (2 min.). Syntheses are performed in simple sintered glass funnels by a single technician. The time required for one synthetic cycle is 20 to 30 minutes and oligodeoxynucleotides containing up to 30 mononucleotides may be obtained in high yields in less than 15 hours.

Whenever possible, the redundancy of the genetic code is capitalized upon to avoid the formation, in any given oligodeoxynucleotide of widely separated base sequences which are the complement of each other, thereby enhancing yields of desired linear strands by avoiding opportunities for the strands to "fold over" on themselves through base complementation.

Purification and isolation of the oligodeoxynucleotide is completed using the following procedure. After the final condensation step including removal of the terminal di-p-anisyl-phenylmethyl group with acid, the silica gels containing the oligodeoxynucleotides are washed thoroughly with methanol and air dried. To remove the methyl group from the phosphotriesters, each polymer (100 mg, containing 2–5 micromoles of oligonucleotide) is treated with 2 ml of thiophenol: $Et_3N$:dioxane (1:2:2) solution for 75 min. at room temperature. This step is followed by treatment with concentrated ammonium hydroxide at 20° C. for 2 hours to hydrolyze the ester joining the oligodeoxynucleotides to the support. After centrifugation and recovery of the supernatant containing the oligodeoxynucleotides the base protection groups are removed by warming in a sealed tube at 50° C. for 24 hours. The ammonium hydroxide solution is then evaporated to dryness. The residue is redissolved in 2 ml of $H_2O$, filtered and the solution then washed three times with n-butanol (3×2 ml). Final purification of the product is by electrophoresis on 20% polyacrylamide gels using a tris-borate buffer (pH 8) containing 7M urea. Approximately 10 O.D. units (260 nm) of the crude material in 30 $\mu$ls of 80% formamide is loaded into a well 2.5 cm wide and electrophoresis is conducted at 16 v/cm. To detect DNA bands, the gel is placed on a fluorescent TLC plate (Sigma Chemical Company) and illuminated with long UV light in order to visualize the oligodeoxynucleotides which appear as intensely absorbing bands in each lane. The desired band is cut from the gel and the DNA eluted with 0.5M ammonium acetate, 10 mM $mgCl_2$, 0.1% SDS, and 0.1 mM EDTA. After two washings with n-butanol, the oligodeoxynucleotides are desalted on a Sephadex G50/40 column (45×2.5 cm) using 10 mM TEAB (ph 7.0). Recoveries from 10 O.D. units of crude DNA generally range from 1.0 to 2.0 O.D. units (260 nm).

The following example specifically illustrates the preparation of oligodeoxynucleotides for use in the manufacture of two genes, one for $\beta_h$-EP and one for the $\beta_h$-EP polypeptide analog, $\beta_h$-[Leu$^5$]-EP.

EXAMPLE 2

With information on hand concerning the amino acid sequence of authentic $\beta_h$-EP (supra), a total of 13 different oligodeoxynucleotides were prepared for use in the manufacture of two genes coding, respectively, for the authentic protein and its [Leu$^5$] analog. Twelve segments including from 18 to 24 mononucleotides and one deoxydecanucleotide were synthesized and isolated according to the general procedures of Example 1.

The eleven segments constructed for use in $\beta_h$-EP gene manufacture had the following sequences.

| | |
|---|---|
| Segment 1En | 5'd(A A T T C C T G C T A T G G T G G C T T T A T G) |

| | |
|---|---|
| Segment 2En | 5'd(A G G T C A T A A A G C C A C C A T A G C A G G) |
| Segment 3En | 5'd(A C C T C C G A A A A G T C T C A G A C T) |
| Segment | 5'd(A G T G G A G T C T G A G A C T T T T C G G) |

3En
| Segment 5En | 5'd(C C A C T G G T T A C T C T G T T T) |
|---|---|
| Segment 6En | 5'd(T T C T T A A A C A G A G T A A C C) |
| Segment 7En | 5'd(A A G A A C G C T A T C A T T A A G A A T G C) |
| Segment | 5'd(T G T A A G C A T T C T T A A T G A T A G C G) |

| | |
|---|---|
| 11En | |

The segments for use in $\beta_h$-[Leu$^5$]-EP gene synthesis included segments 3En through 11En noted above and, in place of segments 1En and 2En, the following segments.

| Segments 1'En | 5'd(A A T T C C A T G T A T G G A G G C T T T C T G) |
|---|---|
| Segment 2'En | 5'd(A G G T C A G A A A G C C T C C A T A C A T G G) |

It will be readily apparent that the odd-numbered segments (except for segment 11En) include the total (top strand) codon sequence needed for synthesis of the 32 amino acid protein, while the even-numbered sequences jontly comprise the complementary bottom strand.

The development of the above oligodeoxynucleotides was the initial step in a basic plan for the synthesis of $\beta_h$-EP and $\beta_h$-[Leu$^5$]-EP set out in Table II below.

TABLE II

DUPLEX D

```
                                          1
              Asn  Ser  Cys  Tyr  Gly  Gly  Phe
        AATTGAATTCAATTCCTGCTATGGTGGCTTT
            CTTAAGTTAAGGACGATACCACCGAAA
                        ―――2―――
         EcoRI 5                    10
              Met  Thr  Ser  Glu  Lys  Ser  Gln  Thr
                              ―3―
              ATGACCTCCGAAAAGTCTCAGACT
              TACTGGAGGCTTTTCAGAGTCTGA
                                 ―――4―――

15                    20
          Pro  Leu  Val  Thr  Leu  Phe  Lys  Asn  Ala  Ile
                       ―5―                        ―7―
          CCACTGGTTACTCTGTTTAAGAACGCTATC
          GGTGACCAATGAGACAAATTCTTGCGATAG
                         ―――6―――

25                    30
              Ile  Lys  Asn  Ala  Tyr  Lys  Lys  Gly
                                        ―9―
              ATTAAGAATGCTTACAAGAAGGGC
              TAATTCTTACGAATGTTCTTCCCG
              ―――8―――              ―――10―――

Glu  Stop  Stop
              GAATGATAGAATTGAATTC
              CTTACTATCTTAACTTAAGTTAA
```

DUPLEX E

```
                    EcoRI
                    1                    5
              Tyr  Gly  Gly  Phe  Leu
              ―1'―
        AATTCCATGTATGGAGGCTTTCTG
           GGTACATACCTCCGAAAGACTGGA"    "
              ―――2'―――
```

| | |
|---|---|
| Segment 8En | 5'd(T T A C A A G A A G G G C G A A T G A T A G) |
| Segment 9En | 5'd(A A T T C T A T C A T T C G C C C T T C T) |
| Segment 10En | 5'd(A A T T G A A T T C) |

It is noteworthy that the above plan calls for the use of ten major oligodeoxynucleotides for the assembly of a gene coding for a 31 amino acid polypeptide. In a very recently published procedure for manufacture of a gene coding for a ten amino acid α-neo-endorphin polypeptide required use of ten oligonucleotides. See, Tanaka, et al., *Nucleic Acids Research*, 10, pp. 1741–1754 (1982).

In general, codons were selected according to endogenous frequency analysis indicating codon preferences of *E. coli*. See, e.g., the Grantham, et al. publications cited supra. In addition to providing a codon sequence translatable into the β-endorphin amino acid sequence, terminal sequences were designed for the purpose of facilitating incorporation of the final product into an *E. coli* transforming vector. In this respect, terminal sequences were provided which would allow insertion of the DNA sequences into one of two EcoRI restriction sites within the β-galactocidase gene of a pBR322 plasmid. Plasmid restriction site locations were, respectively, 24 and 3018 base pairs downstream of the initial methionine-specifying codon of the β-galactosidase gene allowing easy formation of β-galactoidase/$β_h$-EP and β-galactocidase/$β_h$-[Leu$^5$]-EP fusion genes coding for synthesis of corresponding fusion proteins.

The following example illustrates the enzymatic joining of the oligonucleotides synthesized in Example 2.

EXAMPLE 3

Figure 1:
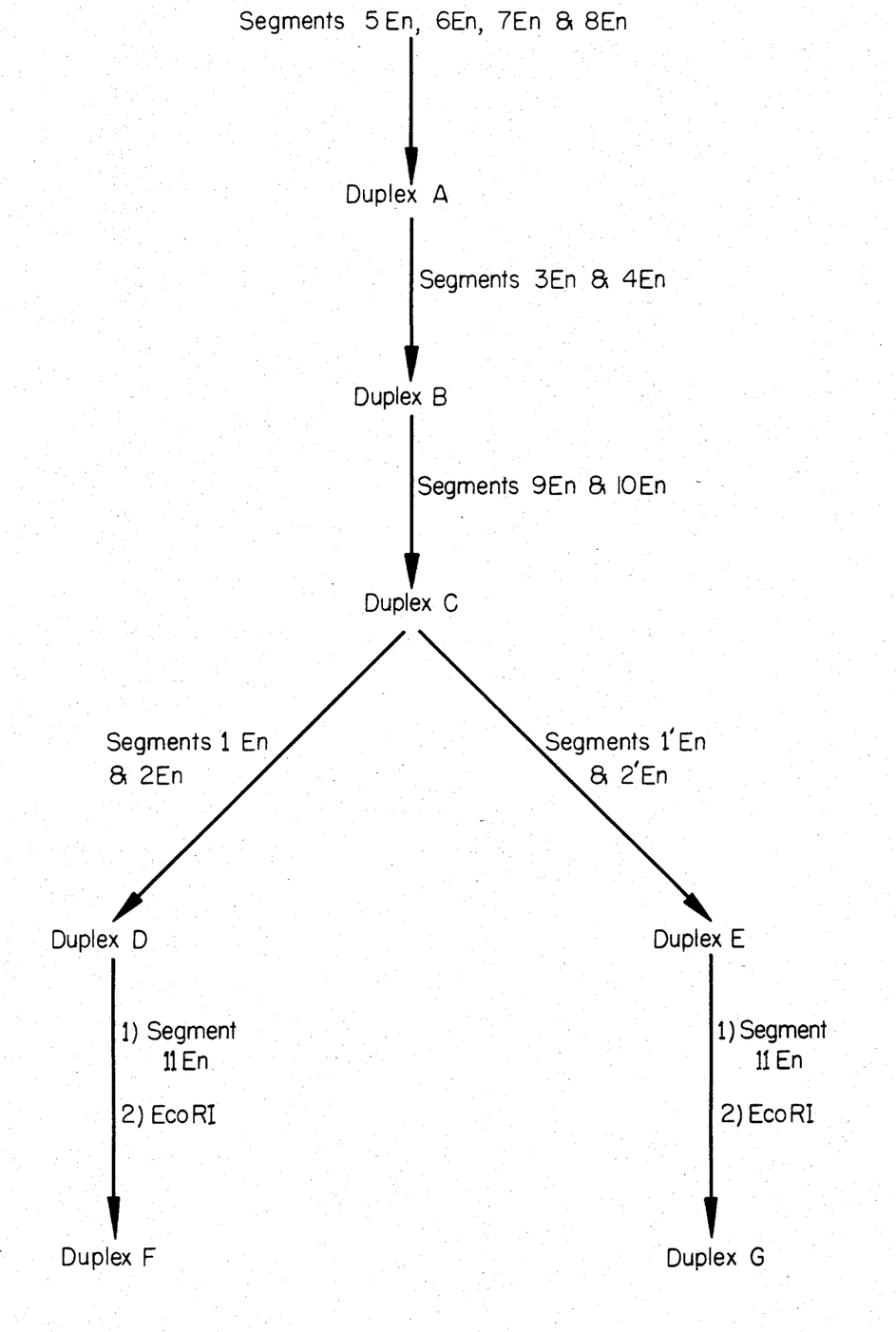
The FIGURE shows the general plan for synthesizing linear, double stranded DNA sequences encoding $\beta_h$-EP ("Duplex D") and $\beta_h$-[Leu$^5$]-EP ("Duplex E").

The general plan for synthesizing linear, double stranded DNA sequences coding for $β_h$-EP ("Duplex D") and $β_h$-[Leu$^5$]-EP ("Duplex E") are outlined in the Drawing.

Also shown in the Drawing are the procedures for converting duplex D to F and duplex E to G. Duplexes F and G code for human β-endorphin and [Leu$^5$] analog thereof respectively when fused to the β-galacosidase gene at the EcoRI site 3018 base pairs from the amino terminal methionine; whereas, duplexes D and E code for human β-endorphin and leu$^5$ analog thereof respectively when fused to the EcoRI site 24 base pairs beyond the amino terminal methionine of β-galactosidase. The general strategy, therefore, begins by the enzymatic joining of segments 5En, 6En, 7En, and 8En to form duplex A. This duplex was then converted to duplex B by the addition of segments 3En and 4En. Duplex B was then converted to duplex C by the addition of segments 9En and 10En. Duplex C contains the DNA segments common to both human β-endorphin and [Leu$^5$] analog thereof. By enzymatic addition of segments 1En and 2En to duplex C, the final 118 base pair duplex, duplex D, coding for human β-endorphin was formed. Similarly, addition of segments 1'En and 2'En to duplex C resulted in the formation of duplex E which codes for the [Leu$^5$] analog of human β-endorphin.

Duplexes D and E can be used directly (after 5'-phosphorylation) for cloning with plasmids such as pPC02. This plasmid contains the lac operon promoter and operator and a single EcoRI site for inserting DNA within the β-galactosidase gene (24 base pairs downstream form the initial methionine codon of the β-galactosidase gene fragment). However, other plasmids such as pBGF120, pEW19, and pBR322 containing the 4.4 kilobase EcoRI fragment from plac5(UV5) with the lac promoter and operator and a single EcoRI site for inserting DNA within the β-galactosidase gene (3018 base pairs from the initial methionine codon of the β-galactosidase gene) offer an advantage in the isolation of the β-galactosidase-β-endorphin fuse polypeptide in that they code for a larger portion of the β-galactosidase gene and hence the resulting fused protein will be larger, and less likely to be digested by the *E. coli* protease. However, in order to capitalize on this advantage, the reading frames of the two fused genes must be such that the translation of the fused gene leads to the desired fused protein. This is not the case here. To overcome this problem, a oligodeoxynucleotide, d(A-A-T-T-G-A-A-T-T-C), was synthesized and ligated with duplexes D and E. This was followed by EcoRI digestion of the ligation products to yield 118 base pair duplexes with the correct reading frames for β-endorphin. These duplexes are labeled F and G for human β-endorphin and the [Leu$^5$] analog thereof, respectively. Specific outlines of the experiments completed in order to synthesize duplexes D, E, F and G are give below.

A. Procedure For Labeling Oligodeoxynucleotides

The oligodeoxynucleotides (1 nmole) were dissolved (34 μl) in 50 mM of HEPES (ph 7.6), 10 mM MgCl$_2$, 10 mM DTT and [γ$^{32}$-P]ATP (2 nmole, specific activity=2–5×10$^3$ cpm/pmole) and incubated with 1 unit of T4-polynucleotide kinase for 40 minutes at 37° C. The reaction mixture was warmed to 70° C. for 5 minutes to inactivate the enzyme. For ligation reactions, the phosphrylated oligodeoxynucleotides were used directly without further purification. In the following discussion, [5'-$^{32}$P] denotes a phosphate radioactively labeled at the 5' end of the oligodeoxynucleotides. If a segment is listed without the [5'-$^{32}$] prefix (i.e., 1En), the segment contains a 5'-hydroxyl group rather than a 5'-phosphate.

B. Enzymatic Joining Of Segments 5En, 6En, 7En, And 8En To Form Duplex A

[5'-$^{32}$P]5En and [5'-$^{32}$P]6En (500 pmole each) were lyopholized to dryness in a 1.5 ml Ependorff tube. The oligodeoxynucleotides were dissolved in 30 μl of 50 mM HEPES (ph 7.6), 10 mM MgCl$_2$, and 10 mM DTT. In a second tube, [5'-$^{32}$P]7En and [5'-$^{32}$P]8En (500 pmole each) were dissolved in 30 μl of the same buffer. The two tubes were warmed in a boiling water bath for 1 minute and slowly cooled to room temperature. The two mixtures were combined and the volume adjusted to 100 μl with the above buffer. The solution was next warmed at 45° C. for 2 minutes and cooled to 4° C. The concentration of ATP was adjusted to 150 mM. After addition of 2 μl of 1.0 m DTT and 5 units of T4-DNA ligase, the mixture was incubated for 18 hours at 4° C. The reaction was monitored by electrophoresis on a 12% polyacrylamide gel using a tris-borate buffer (ph 8.0) containing 7M urea. After 18 hours, the reaction was considered complete and the reaction solution was used directly for preparing duplex B.

C. Enzymatic Joining of Segments 3En and 4En to Duplex A

[5'-$^{32}$P]3En and [5'-$^{32}$P]4En (500 pmole each) were combined and dissolved in 50 μl of 50 mM HEPES (ph 7.6), 10 mM MgCl$_2$, and 10 mM DTT. The mixture was warmed in a boiling water bath for 1 minute and slowly cooled to room temperature. This solution was then transferred to the ligation mixture containing duplex A. This combined solution was warmed at 40° C. for 2 minutes and then cooled to 4° C. The ATP concentration was adjusted to 150 μM and 2 μl of 1M DTT was added. Following the addition of 5 units of T4-DNA ligase, the reaction mixture was incubated for 15 hours at 4° C. An aliquot (0.5 μl) was analyzed by electrophoresis on a 12% polyacrylamide gel. The results of this analysis indicates that duplex B was formed. Duplex B was purified from the starting materials and various intermediate products by column chromatography on Sephadex G150/40 (28×0.5 cm) using 10 mM triithylammonium bicarbonate (ph 7.5) as the buffer. Fractions containing duplex B were pooled and used for the preparation of duplex C.

D. Enzymatic Joining of Segments 9En and 10En To Duplex B To Form Duplex C

Duplex B (180 pmole) was dissolved in 22 µl of 50 mM HEPES (ph 7.6), 10 mM MgCl$_2$, and 10 mM DTT. In a second tube, [5'-$^{32}$P]9En and 10 En (360 pmole each) were dissolved in 55 mM HEPES, 11 mM MgCl$_2$ and 11 mM DTT (22 µl) and the solution warmed in a boiling water bath for 1 minute. After cooling to room temperature, the solution was transferred to the tube containing duplex B. The combined solutions were warmed at 45° C. for 5 minutes and then slowly cooled to 4° C. Next, ATP was added to a final concentration of 250 µM. After the addition of 1 µl of 1M DTT and 5 units of T4-DNA ligase, the reaction mixture was incubated for 15 hours at 4° C. An aliquot (0.5 µl) was analyzed by electrophoresis on polyacylamide gels. The results of this analysis indicated that duplex C was formed.

E. Enzymatic Joining Of Segments 1En and 2En To Duplex C To Form Duplex D And Of Segments 1'En and 2'En to Duplex C to Form Duplex E The ligation mixture (50 µl) containing duplex C was divided into two equal parts of 25 µl each. [5'-$^{32}$P]2En and 1En (180 pmole each, preannealed as described were added to one part. [5'-$^{32}$P]2'En and 1'En (180 pmole each, preannealed as previously described) were added to the second part. These reaction mixtures were warmed at 37° C. for 2 minutes and then slowly cooled to 4° C. T4-DNA ligase (5 units) was added to each tube and the ligation mixtures were incubated at 4° C. for 15 hours. Aliquots (0.5 µl) were removed and analysed by electrophoresis on polyacrylamide gels. The correct duplexes appear to have been formed. The ligation mixtures were desalted on a Sephadex G150/40 (28×0.5 cm) column using 10 mM triethylammonium bicarbonate (ph 7.6) as buffer. This step also eliminated the starting monomers from the ligation mixture but not intermediate duplexes such as unreacted C. The calculated yields of duplexes D and E were 45 and 42 pmole respectively.

F. Enzymatic Joining Of Segment 11En to Duplex D To Form Duplex F

Duplex D (8 pmole) and 500 pmole of segment 11En were phosphorylated using [γ-$^{32}$P] ATP (2 nmole) and T4-polynucleotide kinase (1 unit). The reaction mixture (20 µl) contained 50 mM HEPES, 10 mM MgCl$_2$, and 10 mM DTT. AFter 50 minutes at 37° C., the reaction mixture was warmed to 65° C. for 15 minutes and then slowly cooled to 4° C. T4-DNA ligase (5 units) and 1M DTT (0.5 µl) were added and the mixture was incubated at 4° C. for 15 hours. The DNA was then precipitated by addition of M sodium acetate (3 µl) and ethanol (500 µl) and storage overnight at −20° C. The supernatant was discarded and the residue was redissolved in 200 µl of 20 mM Tris- HCl (ph 7.5), 7 nM MgCl$_2$, 2 mM 2-mercapthoethanol, and 50 mM NaCl. EcoRl (50 units) was next added and the reaction allowed to proceed for 4 hours at 37° C. Aliquots were removed every hour and the extent of reaction was monitored by electrophoresis on a polyacrylamide gell. After 4 hours, the reaction was complete. The EcoRl reaction mixture was next warmed at 65° C. for 15 minutes and then desalted on a Sephadex 150/40 column. Duplex G can be prepared by a similar procedure using duplex E and Segment 11En.

Duplexes F and G were cloned in *E. coli* using plasmids M13mp8 and M13mp7, respectively. These plasmids were obtained from the Bethesda Research Laboratories, Inc. The proposed structure of the duplexes was verified by sequencing of the cloned DNA. The sequencing results confirmed that the top strand of Duplex F had the following sequence:

A-A-T-T-G-A-A-T-T-C-A-A-T-T-C-C-T-G-C-T--
A-T-G-G-T-G-G-C-T-T-T-A-T-G-A-C-C-T-C-C-
-G-A-A-A-A-G-T-C-T-C-A-G-A-C-T-C-C-A-C--
T-G-G-T-T-A-C-T-C-T-G-T-T-T-A-A-G-A-A--
C-G-C-T-A-T-C-A-T-T-A-A-G-A-A-T-G-C-T--
T-A-C-A-A-G-A-A-G-G-G-C-G-A-A-T-G-A-T-
A-G-A-A-T-T-G-A -A-T-T-C;

and that the top strand of Duplex G had the following sequence:

A-A-T-T-G-A-A-T-T-C-A-A-T-T-C-C-A-T-G-T--
A-T-G-G-A-G-G-C-T-T-T-C-T-G-A-C-C-T-C--
C-G-A-A-A-A-G-T-C-T-C-A-G-A-C-T-C-C-A--
C-T-G-G-T-T-A-C-T-C-T-G-T-T-T-A-A-G-A--
A-C-G-C-T-A-T-C-A-T-T-A-A-G-A-A-T-G-C--
T-T-A-C-A-A-G-A-A-G-G-G-C-G-A-A-T-G-A-
T-A-G-A-A-T-T-G-A -A-T-T-C.

While the foregoing procedure involved more or less sequential assembly of double stranded DNA sequences which contain relatively long duplex regions and relatively short single stranded regions, a cursory examination of the variations in the base sequences of single stranded regions reveals that the entire joining procedure may be carried out in a single, "shotgun", reaction.

The following example illustrates procedures for the insertion of the above-noted Duplex E into a microorganism transformation vector; the use of such a vector in the transformation of *E. coli* host cells; the growing, under appropriate nutrient conditions, of transformed *E. coli* cells; the isolation of fused protein products from cultured growth of the cells; and the isolation and testing biological activity of β$_h$-[Leu$^5$]-EP expressed.

EXAMPLE 4

The vector chosen for expression was a pBR322/λplac derivative utilizing all of pBR322 minus a small HindIII to EcoRI fragment. It also contains the promoter region for β-lactamase. This vector was designated pBR-lac. The vector was cleaved with EcoRI and duplex E was ligated thereinto with T4 ligase to form a hybrid called BEL I.

Expression was demonstrated by growing *E. coli* cells transformed with pBR-lac and BEL I on AMP (20 µg/ml) plates overnight and then picking single colonies into 10 ml of L broth and growing at 37° C. in a shaker at 250–300 rpm for 8 hours. Serial dilutions of the 8 hour cultures were plated out on L plates and AMP plates (20 µg/ml) to determine plasmid loss. Five milliliters of cells of both types were centrifuged and the pellet was resuspended in 70% formic acid/cyanogen bromide (5 mg/ml) and allowed to stand at 4° C. for 30 to 48 hours. The samples were washed, lyophilized and resuspended in 1 ml of acetic acid. Suitably prepared samples were tested in a radioimmunoassay for human β-endorphin (Kit No. 1600 , Immuno Nuclear Corp., Stillwater, Minn.). Negative controls (no protein and protein from *E. coli* transformed with the nonhybridized vector) showed little or no inhibition of antibody binding to the $^{125}I$ labelled standard, while the protein from the BEL I transformed cells was for beyond the range of the standard curve.

While the above examples illustrate the preparation of only one polypeptide analog of $\beta_h$-EP, it is clear that the present invention provides the basis for the preparation of numerous other analogs which differ from the authentic protein in terms of the identity or relative position of one or more amino acids. An example of such an analog is $\beta_h$-[Trp$^{27}$]-EP which was noted in the Li, et al. publication, supra, to possess increased analgesic potency and decreased receptor binding activity vis-a-vis the authentic protein. Preparation of this analog may be accomplished by the above-noted procedures for synthesis of authentic $\beta_h$-EP with the single exception that, when preparing segment 9En, the codon TGG would replace the codon TAC (e.g., the first five nucleotides in segment 9En would read TTGGA rather than TTACA). Corresponding alteration of the base sequence in segment 8En would be made.

Products of the present invention and/or their antibodies thereto may be suitably "tagged", for example radiolabelled (e.g., with $^{125}I$) conjugated with enzyme or fluorescently labelled to provide reagent materials useful in assays and/or diagnostic test kits, for the qualitative and/or quantitative determination of the presence of such products and/or said antibodies in fluid samples. Such antibodies may be obtained from the innoculation of one or more animal species (e.g., mice, rabbit, goat, human, etc.) or from monoclonal antibody sources. Any of such reagent materials may be used alone or in combination with a suitable substrate, e.g., coated on a glass or plastic particle or bead.

Numerous modifications and variations in the practice of the invention are expected to occur to those skilled in the art upon consideration of the foregoing illustrative examples. Consequently, the invention should be considered as limited only to the extent reflected by the appended claims.

What is claimed is:

1. A method for synthesis of linear, double stranded DNA sequences from nucleotide bases comprising the steps of:
   (1) synthesizing from nucleotide bases two or more different, linear, duplex DNA strands, each duplex strand comprising a double stranded region of 12 or more selected complementary base pairs and further comprising at least one single stranded terminal sequence of from 3 to 7 selected bases at one end of the strand, each single stranded terminal sequence of each duplex DNA strand comprising the entire base complement of at most one single stranded terminal sequence of any duplex DNA strand prepared; and
   (2) annealing and ligating each duplex DNA strand prepared in step (1) to one or two different duplex strands prepared in step (1) having a complementary single stranded terminal sequence, thereby to form a single continuous double stranded DNA sequence which has a duplex region of at least 27 selected base pairs comprising at least 3 base pairs formed by complementary association of single stranded terminal sequences of duplex DNA strands prepared in step (1) and which has from 0 to 2 single stranded terminal regions of from 3 to 7 bases.

2. A method according to claim 1 wherein at least three different duplex DNA strands are prepared in step (1) and all strands so prepared are annealed and ligated concurrently in a single annealing and ligating reaction mixture to form a single continuous double stranded DNA sequence which has a duplex region of at least 42 selected base pairs comprising at least two non-adjacent sets of 3 or more base pairs formed by complementary association of single stranded terminal sequences of duplex strands prepared in step (1).

3. A method according to claim 1 wherein the duplex DNA strand preparation step (1) comprises the steps of:
   (a) constructing first and second linear oligodeoxynucleotide segments having 15 or more bases in a selected linear sequence, the linear sequence of bases of said second segment comprising the total complement of the sequence of bases of said first segment except that at least one end of said second segment shall either comprise an additional linear sequence of from 3 to 7 selected bases beyond those fully complementing said first segment, or shall lack a linear sequence of from 3 to 7 bases complementary to a terminal sequence of said first segment, provided, however, that said second segment shall not have an additional sequence of bases or be lacking a sequence of bases at both of its ends; and,
   (b) combining said first and second segments under conditions conducive to complementary association between segments to form a linear, duplex DNA strand.

4. A method according to claim 1 wherein the continuous double stranded DNA sequence formed in step (2) comprises an entire structural gene expressable in a selected host microorganism as a composition comprising a biologically functional protein.

5. A method according to claim 4 wherein, in the double-stranded DNA sequence formed, the sequence of bases comprises one or more codons selected, from among alternative codons specifying the same amino acid, on the basis of preferential expression characteristics of the codon in a projected host microorganism.

6. A method according to claim 1 further comprising the step of labelling the double-stranded DNA sequence formed in step (2) with a detectable signal for use as a reagent material.

7. The method according to claim 6 wherein said signal is $^{125}I$.

* * * * *

UNITED STATES PATENT AND TRADEMARK OFFICE
CERTIFICATE OF CORRECTION

PATENT NO. : 4,652,639

DATED : March 24, 1987

INVENTOR(S) : Yitzhak Stabinsky

It is certified that error appears in the above-identified patent and that said Letters Patent is hereby corrected as shown below:

At Column 1, line 65 please delete "seqeunces" and insert -- sequences -- therefor;

At Column 1, line 37 please delete "uricil" and insert -- uracil -- therefor;

At Column 4, line 55 please delete "pair" and insert -- pairs -- therefor;

At Column 7, line 67 please delete "8-endorphin" and insert -- β-endorphin -- therefor;

At Column 8, line 1 please delete "8-endorphin" and insert -- β-endorphin -- therefor;

At Column 13, line 15 please delete "3" and insert -- 4 -- therefor;

At Column 15, lines 29-30 please delete "β-galacosidase" and insert -- β-galactosidase -- therefor;

At Column 16, line 10 please delete "give" and insert -- given -- therefor; and

UNITED STATES PATENT AND TRADEMARK OFFICE
CERTIFICATE OF CORRECTION

PATENT NO. : 4,652,639

DATED : March 24, 1987

INVENTOR(S) : Yitzhak Stabinsky

It is certified that error appears in the above-identified patent and that said Letters Patent is hereby corrected as shown below:

At Column 17, line 53 please delete "AFter" and insert -- After -- therefor.

Signed and Sealed this

Twenty-fourth Day of July, 1990

Attest:

HARRY F. MANBECK, JR.

*Attesting Officer*　　　　　*Commissioner of Patents and Trademarks*